United States Patent [19]

Giaever et al.

[11] Patent Number: 4,920,047
[45] Date of Patent: Apr. 24, 1990

[54] ELECTRICAL DETECTION OF THE IMMUNE REACTION

[75] Inventors: Ivar Giaever, Schenectady; Charles R. Keese, Schoharie, both of N.Y.

[73] Assignee: General Electric Company, Schenectady, N.Y.

[21] Appl. No.: 196,718

[22] Filed: May 20, 1988

[51] Int. Cl.$^5$ ............................................. G01N 33/53
[52] U.S. Cl. ........................................... 435/7; 435/4; 435/28; 435/817; 204/403; 436/806
[58] Field of Search ............... 435/817, 7, 4; 204/403; 436/525, 806

[56] References Cited

U.S. PATENT DOCUMENTS 4,054,646 10/1977 Giaever .
4,072,576 2/1978 Arwin et al. .
4,151,049 4/1979 Janata .
4,490,216 12/1984 McConnell .

Primary Examiner—Sam Rosen
Attorney, Agent, or Firm—Mary A. Montebello; James C. Davis, Jr.; William H. Pittman

[57] ABSTRACT

Test method and apparatus for determining the presence of, the concentration of, or the absence of, immunologically-active substances in liquid media by measuring any change of electrical impedance of an electrode due to the presence of, or the absence of, the reaction of a product of enzyme linked immunologically-active substance and a proper enzyme substrate.

9 Claims, 3 Drawing Sheets

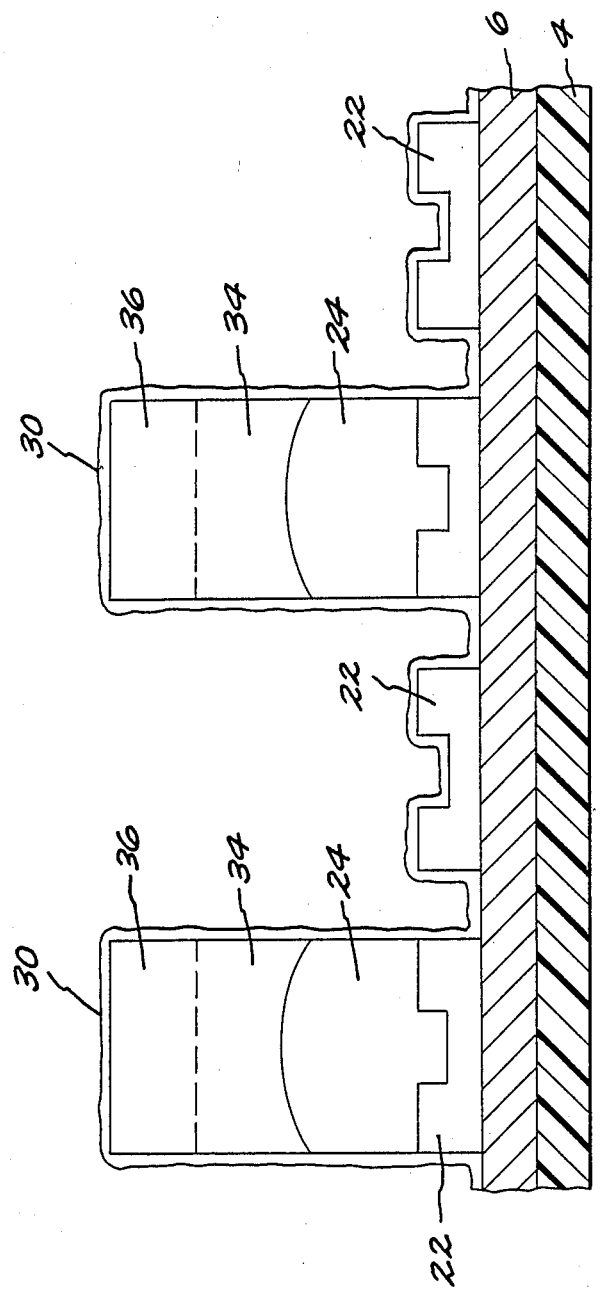

ELECTRICAL DETECTION OF THE IMMUNE REACTION

FIELD OF THE INVENTION

This invention relates to a test method and an apparatus for the detection of immunologically active substances. More particularly, this invention relates to the detection of antibodies and antigens through electrical means.

BACKGROUND OF THE INVENTION

Immunological reactions are highly specific interactions in which an antigen binds with a corresponding constituent specific to the antigen and generally known as the antibody, to form an immunological complex. In a biological system, the entry of a foreign biological constituent causes the biological system to produce the specific antibody to the antigen. The antibody molecules have chemical binding sites which compliment those on the antigen molecules so that the antigen and the antibody bond to form the immunological complex.

Antibodies are produced by biological systems in response to invasion thereof of foreign bodies. Even the antibody of one system can act as an antigen in another system and invoke an immunological reaction.

Consequently, the detection of either antigens or antibodies present in a biological system is of medical diagnostic value in determining which antigens are present or to which antigens the system has been exposed.

Most antigens are proteins or contain proteins as an essential part, whereas all antibodies are proteins. An antigen and an antibody protein may each have several binding sites.

Additional immunological reactions other than antigen-antibody reactions are also contemplated by the invention. For instance, the following systems include biological particles which are capable of undergoing the immunological reactions described herein:
Viruses
Bacteria and Bacterial Toxins
Fungi
Parasites
Animal Tissue
Animal Body Fluids and the like.

An illustration of antigens would be goat antibody, human chorionic gonadotrophin (HCG) and hepatitis associated antigen (HAA).

Antigens, with respect to viruses, are viral particles, and the corresponding antibody is produced by administration of the antigen to a living host. Illustrations of such antigen-antibody complexes useful in the herein disclosed invention are: Rubella virus antigens—Rubella virus antibody; polio virus antigen—polio virus antibody; versicular stomatitis virus (VSV) antigen—VSV antibody, and acquired immune deficiency syndrome (AIDS) antigen—AIDS antibody.

Antibodies corresponding to bacteria and bacterial toxins are produced in a manner similar to virus antibodies. The following are illustrative examples of bacteria or bacteria toxin antigen—antibody pairs which can be used in the present invention: tetanus toxoid suspension (antigen)—tetanus antibody; diphtheria toxin suspension (antigen)—diphtheria antibody; Neisseria genorrhoea suspension (antigen)—gonorrhoea antibody; *Treponema palladium* suspension (antigen)—syphilis antibody.

Fungi antigens are antigenic extracts of fungal suspensions, and the antibody is the fungal antibody produced by introduction into a living host. Illustrations of fungi system antigen-antibody complexes are: Aspergillus extract suspension (antigen)—aspergillus fungus antibody; Candida extract suspension (antigen)—candida fungus antibody.

Antigens and antibodies in parasite systems are tested in a similar manner. The system *Toxoplasma gondii* extract (antigen)—*Toxoplasma gondii* antibody is exemplary.

Polysaccharide is a system wherein the antigen is a carbohydrate antigen such as the antigen—antibody system of pneumococcus polysaccharides (antigen)—pneumococcus antibody.

The antigenic constituent with respect to hormones is usually found in a hormone extract, and the antibody is the particular hormone antibody elaborated by the living organism after injection. An illustration of this antigen-antibody complex is insulin-hormone-insulin antibody.

Specific antigens or antibodies can also be labeled with an enzyme. Typically, in an enzyme-linked surface-immuno-assay [ELISA], the antigen is adsorbed to a surface in a little well. The sample suspected of containing antibody is added to the well and allowed to incubate. If the sample contained antibody, some of the antibody will have specifically attached to the preadsorbed antigen. The well is then rinsed and a second antibody linked to an enzyme is added to the well. This second antibody may be specific for either the antigen or for the first antibody but not for both. If the second antibody is specific for the antigen, this is called a competition assay. If the second antibody is specific for the antibody, this is called a sandwich assay. The well is again rinsed, and the proper substrate for the enzyme is added to the well. The enzyme, if present, will react with the substrate, typically in such a manner that the color of the solution changes. The change in color is accordingly correlative to the amount of antibody in the first solution.

Certain other enzymes will cause a precipitate to form, and the detection of, the presence of, and the amount of that precipitate will indicate the presence of and the concentration of the antibody suspected in first solution.

Arwin et al., U.S. Pat. No. 4,072,576 studied enzymatic reactions by measuring the electrical potential difference over membranes specific for the reaction product of the reaction between an enzyme and a specific substrate for that enzyme. Such a method is not broadly applicable to a wide variety of immunologically-active substances.

In Giaever, U.S. Pat. No. 4,054,646, such immunological reactions are shown to take place on a metal globule-coated substrate. The resultant antigen-antibody complex can then be examined by optical means, and by contrasting the thickness of the bare antigen or antibody with the thickness of the antigen-antibody complex. In McConnell, U.S. Pat. No. 4,490,216, such antigen-antibody complexes may be detected by changes in electrostatic interaction between a polarity layer and an amphiphilic layer linked to the antigen-antibody complex and separated from the polarity-sensitive layer by a lipid layer. In Janata, U.S. Pat. No. 4,151,049, detection of the presence of chemical substances is accomplished by measuring the change in electrical charge of an electrode encased with a membrane comprising a hydrophobic organic polymeric substrate with hydrocarbon chains with specific proteins (antigen or antibodies) adsorbed thereon. A long time—of the order of one to two days—is required to complete the measurement.

It is the object of the present invention to detect, more quantitatively, and by electrical means, the immune reaction by use of enzyme-linked immunologically-active substances and the enzyme-substrate reaction.

A primary advantage of the present invention is the simplicity of the electrical measurements employed. A further advantage is that the procedure can be carried out rapidly. In another advantageous embodiment, several electrodes may be used in a single liquid medium to be analyzed for the presence of several immunologically-active substances. This permits many different immunologically-active substances to be analyzed at the same time.

BRIEF DESCRIPTION OF THE DRAWINGS

FIG. 4 is an elevation view of the apparatus of FIG. 2 illustrating the steps involved in making and using the same in an embodiment comprising a sandwich assay.

SUMMARY OF THE INVENTION

Figure 1:
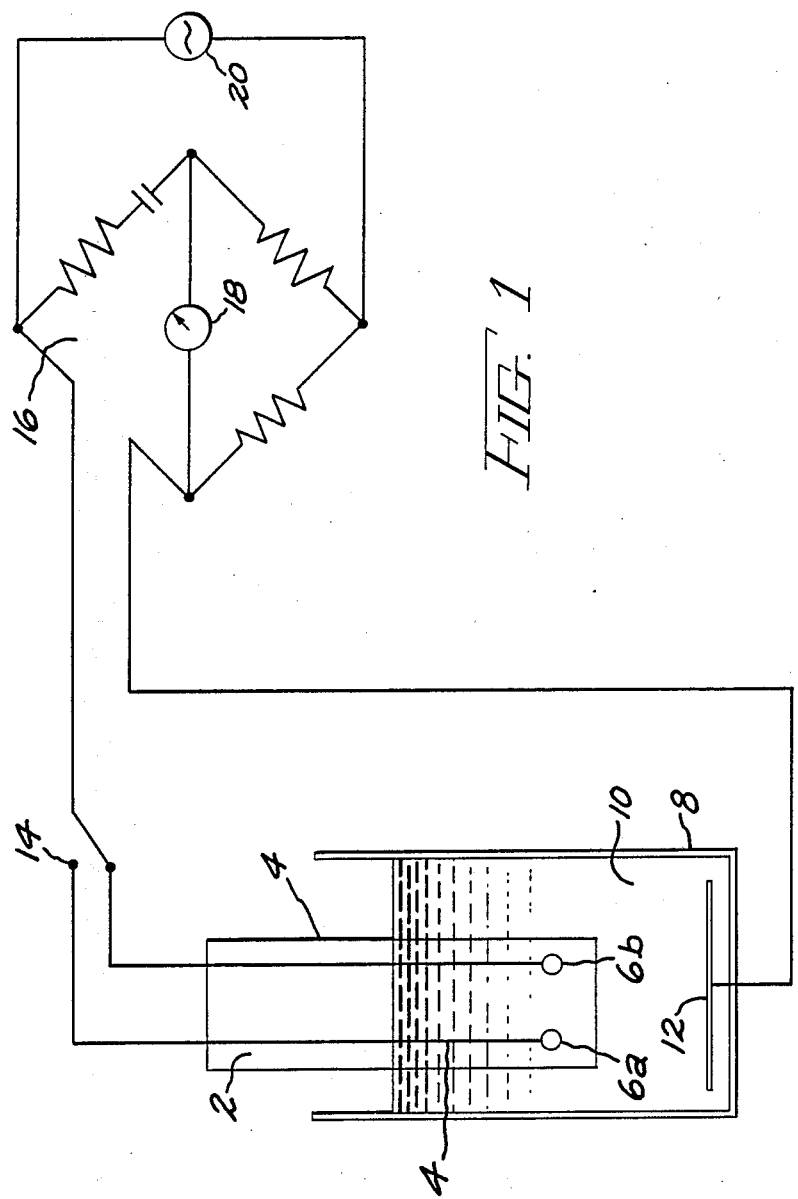
FIG. 1 illustrates in diagrammatic form an electrode apparatus and means for detecting the immune reaction by measuring the impedance of the electrode in accordance with the present invention.

This invention provides a method for quantitative detection of the presence of an immunologically active substance by measurement of the change in impedance of an electrode having (a) bonding-sites specific for the substance and (b) an enzyme-carrying reagent in a media which comprises a substrate for the enzyme which can react with the enzyme to form an insoluble reaction product which, upon formation, coats at least part of the electrode thereby varying its impedance.

In general, the electrode of this invention comprises a chemically and electrically inert material, such as plastic, glass, ceramic or the like, on which a thin metal film has been deposited. The metal film, in turn, is provided with an immunologically active substance, such as an antigen or an antibody, adsorbed onto at least a portion of the metal film surface. This immunologically reactive substance provides binding sites for formation of an immunological complex thus preventing further binding at an already occupied site. The resulting existence or nonexistence of available binding sites can be utilized in a quantitative method for inducing a variation in the impedance of the electrode by exposing it to a reagent which can react to form an insoluble reaction product with deposits and adheres to the metal film thereby causing a change in impedance. The reagent is an enzyme-carrying immunologically reactive material which will complex at open binding sites on the electrode thereby fixing the enzyme on the electrode surface. Exposure of the resulting enzyme-active electrode to a suitable reactive substrate for the enzyme will provide the insoluble reaction product which in turn deposits on at least a portion of electrode thereby causing a variation in impedance as measured by the apparatus herein described.

This invention can be described as an antigen or antibody detection and measurement method which is based on an enzyme reaction at unoccupied binding sites of the antigen or antibody.

According to the present invention, a method is provided for the determining of the presence of, the concentration of, or the absence of, a first immunologically-active substance in a liquid medium, said method comprising the steps of providing an electrode having a small area of from about $10^{-10}$ cm$^2$ to about $10^{-2}$ cm$^2$ on a substrate material, adsorbing a second immunologically-active substance capable of binding the first immunologically-active substance on said electrode, contacting said electrode having the second immunologically-active substance adsorbed thereon with a liquid medium to be analyzed for the presence or absence of the first immunologically-active substance, contacting said electrode with a liquid medium comprising a third immunologically-active substance linked to an enzyme which either is capable of binding with the second immunologically-active substance and incapable of binding with the first immunologically-active substance or is capable of binding with the first immunologically-active substance and incapable of binding with the second immunologically-active substance, contacting said electrode with a liquid medium comprising an enzyme substrate capable of reacting with the enzyme linked to the third immunologically-active substance to form an insoluble reaction product, immersing said electrode into a measuring solution, and measuring the electrical impedance of said electrode. If said third immunologically-active substance linked to an enzyme were of the type capable of binding with said second immunologically-active substance and not capable of binding with said first immunology active substance, no change or a small change in measured impedance indicates that no enzymatic reaction has taken place, and therefore, the suspected said first immunologically-active substance is present. On the other hand, a large change of impedance indicates the absence of the first immunologically-active substance. The degree of change is proportional to the concentration of the first immunologically-active substance in the liquid medium. If the third immunologically active substance were of the type capable of binding with the first immunologically-active substance and incapable of binding with said second immunologically-active substance, no change or a small change in impedance would again indicate that no enzymatic reaction has taken place, as well as also indicating the absence of the first immunologically-active substance. A large change in impedance would indicate the opposite, again with the degree of change being proportional to the concentration of the first immunologically-active substance in said liquid medium. Measured impedance in either assay can be compared to a standard curve of concentration versus impedance and thereby provide a quantitative concentration analysis of the first immunologically-active substance.

Another major aspect of the invention includes, in a first embodiment, apparatus for determining the presence of, the concentration of, or the absence of a first immunologically-active substance, the apparatus comprising an electrode of known impedance having a second immunologically-active substance capable of binding said first immunologically-active substance adsorbed in at least one area on the surface thereof, said area being small and of a size in the range of from about $10^{-10}$ cm$^2$ to about $10^{-2}$ cm$^2$. Also contemplated, as a second embodiment, is an apparatus as first defined above further comprising an immunologically bound layer over a first layer, comprising (i) said first immunologically-active substance, (ii) a third immunologically-active substance linked to an enzyme and capable of ending with said second immunologically-active substance, but incapable of binding with said first immunologically-active substance, or (iii) a mixture of (i) and (ii). In a third embodiment, the invention contemplates apparatus, as first defined above further comprising an immunologically bound layer adsorbed on at least a portion thereon comprising said first immunologically-active substance and said first immunologically-active substance has adsorbed thereon an immunologically bound layer comprising a third immunologically active substance linked to an enzyme and capable of binding with the first immunologically-active substance but incapable of binding with the second immunologically-active substance.

The apparatus comprising the second and third embodiments can further comprise, as an overlayer on the third immunologically-active substance linked to an enzyme, a reaction product of the enzyme and a specific substrate for the enzyme.

DETAILED DESCRIPTION OF THE INVENTION

Referring to FIG. 1, there is illustrated a measuring device to determine changes in impedance on electrode 2 comprising support 4 which can be metal, glass, mica, fused silica, quartz, thermoplastics thermosetting plastics, and the like, preferably an engineering thermoplastic, such as a polycarbonate sheet on which is deposited metal surfaces 6a and 6b comprised of, for example, sputter deposited metal film of, for example, gold, platinum, tantalum, indium, titanium and the like. The electrode 2 is partially immersed in vessel 8 which contains liquid measuring solution 10, such as water or saline solution. Impedance of electrode 2 is measured by use of counter electrode 12, electrically coupled to external impedance bridge 16, detector 18 and alternating current source 20, having a rating of 100–10,000 Hz and voltages of about 0.1 to about 10 millivolts. Generally, the apparatus is operated at a voltage of about 1 millivolt. Also shown is optional switch 14 which permits impedance measurements to be made on alternate metal patches 6a and 6b.

Figure 2:
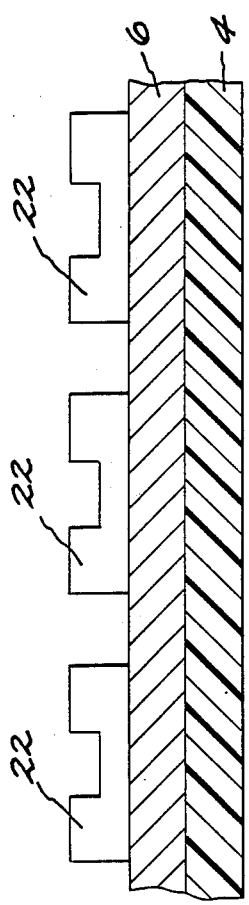
FIG. 2 is an elevation view of an apparatus in accordance with this invention illustrating an electrode with a second immunologically-active substance adsorbed thereon.
Figure 3:
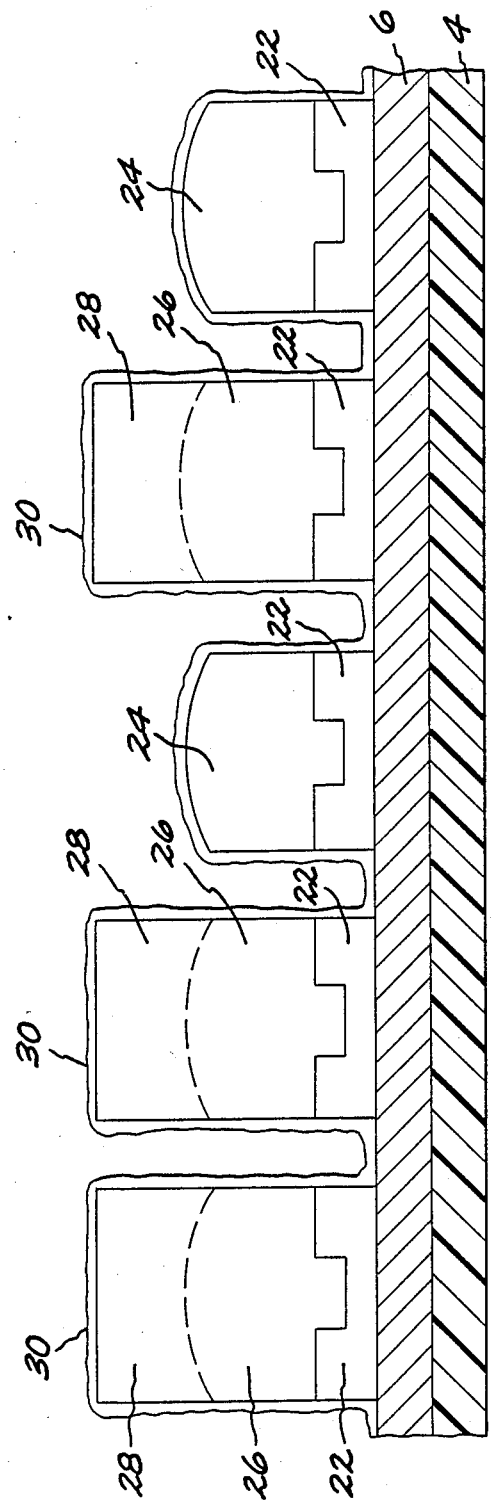
FIG. 3 is an elevation view of the apparatus in FIG. 2 illustrating the steps involved in making and using the same in an embodiment comprising a competition assay.

FIG. 2 illustrates, in schematic form, a cross section through electrode 2 wherein a layer comprising second immunologically-active substance 22 is adsorbed on a portion of a metal film electrode 6 carried on body material 4. The slots shown as part of substance 22 represent binding sites. The immunologically-active substances represented by reference numeral 22 preferably comprise antigens or antibodies, many of which are illustrated herein. FIG. 3 helps illustrate the method and apparatus of this invention when utilizing a competition assay. An electrode of FIG. 2 is immersed in liquid medium which is to be analyzed for the presence of a first immunologically-active substance 24. Because the first immunologically-active substance 24 is specific for second immunologically-active substance 22, units of substance 24 will bind to the binding sites of substance 22 to form an antigen-antibody complex adsorbed onto metal 6 of the electrode. Furthermore, at least a portion and, depending on the concentration, all of the available binding sites shown as slots on substance 22 will be occupied now and be covered by the first immunologically-active substance 24. If, on the other hand, the first immunologically-active substance 24 is absent, nothing will be bound to the second immunologically active substance 22, no antigen-antibody complexes will be formed and no binding sites will be covered. To continue the analysis, the electrode is then contacted with a liquid medium comprising a third immunologically-active substance 26 capable of binding with the second immunologically-active substance 22 but incapable of binding with the first immunologically-active substance 24. Substance 26 is linked to enzyme 28. If the first immunologically-active substance 24 were present in the sample to be tested in concentrations sufficient to saturate the binder sites on said second immunologically-active substance 22, none of the third immunologically-active substance 26 will be able to bind to substance 22 and therefore, no units of substance 26 will remain attached to the electrode. Consequently, no enzyme 28 will be attached to the electrode either. If however, as shown in FIG. 3, the first immunologically-active substance 24 were present in the sample to be tested in relatively low concentration, at least some binder sites of substance 22 would have remained open and some third immunologically-active substance 26 and enzyme 28 will bind to those open binder sites on said second immunologically-active substance 22. As a direct result, some enzyme will become attached to the electrode. If the first immunologically-active substance 24 were absent from the sample to be tested, all of the binder sites on the second immunologically active substance 22 would necessarily be open and available, and the third immunologically-active substance 26 linked to enzyme 28 would bind to each of them. Therefore, enzyme 28 indirectly would be attached through 26 to each of the second immunologically-active substance 22 binding sites. To continue the analysis, the electrode is then contacted with a liquid medium containing an appropriate enzyme substrate for the enzyme linked to the third immunologically-active substance, the enzyme reacting with the enzyme substrate to form an insoluble molecule layer shown as 30 which coats the electrode changing its impedance.

To complete the analysis, the change in impedance of electrodes treated as described resulting from precipitation of layer 30 is determined electrically, for example, in an apparatus shown in FIG. 1.

A small change or no change in impedance indicates that no enzymatic reaction has taken place and therefore that the suspected first immunologically-active substance 24 is present at a level sufficient in the sample to be tested to saturate the binding sites on the second immunologically-active substance 22. On the other hand, a large change of impedance indicates the absence of the first immunologically-active substance in the sample to be tested. Intermediate changes of impedance indicate the presence of the first immunologically-active substance, but in concentrations less than that required to saturate the binder sites on the second immunologically-active substance. The degree of change is proportional to the concentration of the first immunologically-active substance in the sample. The sample is compared to a predetermined standard curve of concentration versus impedance to determine the concentration of the first immunologically-active substance.

If said first immunologically-active substance to be detected by the invention utilizing a competition assay as described above comprises an antibody, said second immunologically-active substance will comprise an antigen and said third immunologically active substance linked to an enzyme will comprise an antibody linked to an enzyme. If said first immunologically-active substance to be detected by the invention utilizing a competition assay as described above comprises an antigen said second immunologically-active substance will comprise an antibody and said third immunologically-active substance linked to an enzyme will comprise an antigen linked to an enzyme.

Illustrative examples of second immunologically-active substances are hepatitis-associated antigen or antibodies. Where the second immunologically-active substance comprises hepatitis-associated antigen, the first immunologically-active substance can comprise a hepatitis-associated antibody, the third immunologically-active substance linked to an enzyme can comprise a hepatitis associated antibody linked to horseradish peroxidase and the enzyme substrate can comprise carbazole and hydrogen peroxide.

FIG. 4 helps illustrate the method and apparatus of this invention utilizing a sandwich assay. If an electrode of FIG. 2 is immersed in a liquid medium which is to be analyzed for a first immunologically-active substance 24 and it is present, because the first immunologically-active substance is specific for the second immunologically-active substance, it will bind to the second immunologically-active substance 22 to form units of an antigen-antibody complex adsorbed onto metal 6 of the electrode. Furthermore, at least a portion of and depending on the concentration, possibly all of the available binding sites shown as slots on the second immunologically-active substance 22 will now be covered by the first immunologically-active substance. If, on the other hand, the first immunologically-active substance is absent, nothing will be bound to the second immunologically-active substance 22, no antigen-antibody complexes will be formed, and no binding sites will be covered.

To continue the analysis, the electrode is optionally, but preferably, rinsed. It is then contacted with a liquid medium comprising an enzyme carrying third immunologically-active substance 34 capable of binding with the first immunologically-active substance 24 but incapable of binding with the second immunologically-active substance 22. If the first immunologically-active substance were absent from the sample to be tested, none of the third immunologically-active substance will be able to bind, and therefore, none will remain attached to the electrode. Consequently, no enzyme 36 will be attached to the electrode either. If, however, first immunologically-active substance were present in the sample to be tested, in relatively low concentrations, at least some of said third immunologically-active substance 34 and enzyme 36 will bind to open binding sites on the first immunologically-active substance shown as curved surfaces on 24. As a direct result, at least some enzyme will be attached to the electrode. To continue the analysis, the electrode material is then contacted with a liquid medium containing a proper enzyme substrate for the enzyme linked to the third immunologically-active substance, and the enzyme reacts with the proper enzyme substrate to form an insoluble molecule layer shown as 30 in FIG. 4.

To complete the analysis, the change in impedance of an electrode prepared as described in comparison with the electrode of FIG. 2 is determined electrically, for example, in an apparatus shown in FIG. 1. However, the absence of a change in impedance would indicate that no enzymatic reaction has taken place, and therefore, that the suspected first immunologically-active substance is absent from the sample to be tested. On the other hand, any change in impedance indicates the presence of the first immunologically-active substance in the sample to be tested, and a large change indicates that the first immunologically-active substance is present at a level sufficient to saturate the binding site on the second immunologically-active substance. The degree of change is proportional to the concentration of the first immunologically-active substance in the sample and is compared to a predetermined standard curve of concentration versus impedance to determine the concentration of the first immunologically-active substance.

If the first immunologically-active substance to be detected by the invention utilizing a sandwich assay as described above comprises an antibody, the second immunologically-active substance will comprise an antigen, and the third immunologically-active substance linked to an enzyme will comprise an antibody linked to an enzyme. If the first immunologically-active substance to be detected by the invention utilizing a sandwich assay as described above comprises an antigen, the second immunologically-active substance will comprise an antibody and the third immunologically-active substance linked to an enzyme will comprise an antibody linked to an enzyme.

DESCRIPTION OF THE PREFERRED EMBODIMENTS

The following example illustrates the invention. The example is not intended to limit the claims in any manner whatsoever.

An electrode is prepared by sputtering or evaporating a gold film on a small area from about $10^{-10}$ cm$^2$ to about $10^{-2}$ cm$^2$, on a polycarbonate substrate. A copper wire is attached to facilitate connecting the gold electrode to an electrical impedance measuring device. Bonine Serum Albumin (BSA) is adsorbed onto the gold electrode. The electrode is then immersed for thirty minutes in a liquid solution suspected of containing anti-BSA-goat antibody. It is removed and rinsed in water. The electrode is then immersed in a solution containing a solution of anti-goat rabbit antibody linked to horseradish peroxidase. The electrode is then removed and placed in a solution containing 3-amino-9-ethyl carbazole and hydrogen peroxide. The electrode is removed and placed in an electrical impedance measuring device. A current of 1000 Hz at 1 millivolt is applied to the device. An increase in impedance is measured, indicating the presence of anti-BSA-goat antibody in the sample solution.

The above-identified patents and test methods are incorporated herein by reference.

Many variations of this invention will suggest themselves to those skilled in this art in light of the above, detailed description. For example, instead of a polycarbonate substrate plated with gold, the electrode can comprise a glass sheet plated with tantalum or indium. Instead of BSA antigen, hepatitis-associated antigen, *Neisseria gonorrhoea* extract (antigen), and AIDS antigen can be adsorbed onto the gold electrode and used to determine, respectively, the presence of, concentration of or absence of corresponding antibodies for hepatitis, gonorrhoea and acquired immune deficiency syndrome. Instead of horseradish peroxidase, alkaline phosphatase can be used as enzymes coupled to the anti-goat antibody. Instead of the aminocarbazole, ortho-tolidine or 3,3'-diamino benzidine can be used as proper substrates for the enzyme. All such obvious modifications are within the full intended scope of the appended claims.

What we claim as new and desire to secure by Letters Patent of the United States is:

1. A method for determining the presence of, the concentration of, or the absence of, a first immunologically-active substance in a liquid medium, said method comprising the steps of:
    (i) providing an electrode comprising a plurality of metal film in a small area, in the range of from about $10^{-10}$ cm$^2$ to about $10^{-2}$ cm$^2$, on a substrate;
    (ii) adsorbing a second immunologically-active substance capable of binding said first immunologically-active substance to said electrode;
    (iii) contacting said electrode having said second immunologically-active substance adsorbed thereon with a liquid medium to be analyzed for said first immunologically-active substance;
    (iv) contacting said electrode with a liquid medium comprising a third immunologically-active substance linked to an enzyme and capable of binding with said second immunologically-active substance and incapable of binding with said first immunologically-active substance;
    (v) contacting said electrode with a liquid medium comprising an enzyme substrate capable of reacting with said enzyme linked to said third immunologically-active substance;
    (vi) immersing said electrode into a measuring solution; and
    (vii) measuring electrical impedance of said electrode whereby no change or only a slight change in impedance indicates the presence of said first immunologically-active substance and a larger change indicates the absence of said first immunologically-active substance, the degree of change being proportional to the concentration of said first immunologically-active substance in said liquid medium.

2. The method of claim 1 wherein said electrode comprises a film of gold, tantalum, indium, platinum, titanium or titanium on a plastic substrate.

3. The method of claim 1 wherein said first immunologically-active substance comprises an antibody, said second immunologically active substance comprises an antigen and said third immunologically-active substance linked to an enzyme comprises an antibody linked to an enzyme.

4. The method of claim 1 wherein said first immunologically-active substance comprises an antigen said second immunologically-active substance comprises an antibody, and said third immunologically-active substance linked to an enzyme comprises an antigen linked to an enzyme.

5. The method of claim 3 wherein said antibody comprises anti-goat antibody, said antigen comprises anti-goat antigen, said antibody linked to an enzyme comprises anti-goat antibody linked to horseradish peroxidase and said enzyme substrate comprises carbazone and hydrogen peroxide.

6. A method for determining the presence of, the concentration, of or the absence of, a first immunologically-active substance in a liquid medium, said method comprising the steps of:
    (i) providing an electrode comprising metal film in a small area, in the range of from about $10^{-10}$ cm$^2$ to about $10^{-2}$ cm$^2$ on a substrate;
    (ii) adsorbing a second immunologically-active substance capable of binding said first immunologically-active substance to said electrode;
    (iii) contacting said electrode having said second immunologically-active substance adsorbed thereon with a liquid medium to be analyzed for said first immunologically-active substance;
    (iv) contacting said electrode with a liquid medium comprising a third immunologically active substance linked to an enzyme and capable of binding with said first immunologically-active substance and incapable of binding with said second immunologically-active substance;
    (v) contacting said electrode with a liquid medium comprising an enzyme substrate capable of reacting with said enzyme linked to said third immunologically-active substance;
    (vi) immersing said electrode into a measuring solution; and
    (vii) measuring the electrical impedance of said electrode whereby no change in impedance indicates the absence of said first immunologically-active substance and any change in impedance indicates the presence of said first immunologically-active substance, the degree of change being proportional to the concentration of said first immunologically-active substance in said liquid medium.

7. The method of claim 6 wherein said electrode comprises globules of gold, tantalum, indium, titanium or titanium on a plastic substrate.

8. The method of claim 6 wherein said first immunologically-active substance comprises an antibody, said second immunologically-active substance comprises an antigen and third immunologically-active substance linked to an enzyme comprises an antibody linked to an enzyme.

9. The method of claim 6 wherein said first immunologically active substance comprises an antigen, said second immunologically-active substance comprises an antibody and said third immunologically-active substance linked to an enzyme comprises an antibody linked to an enzyme.

* * * * *